United States Patent [19]

Schilling, Jr.

[11] 4,049,676
[45] Sept. 20, 1977

[54] SULFOLANYLOXYALKYL CYCLIC POLYSILOXANES

[75] Inventor: Curtis Louis Schilling, Jr., Croton-on-Hudson, N.Y.

[73] Assignee: Union Carbide Corporation, New York, N.Y.

[21] Appl. No.: 592,092

[22] Filed: June 30, 1975

[51] Int. Cl.$^2$ .................... C07D 333/48; B01F 17/00
[52] U.S. Cl. ................................. 260/332.1; 252/351
[58] Field of Search ........ 260/332.1, 448.25, 448.2 H, 260/448.2 N

[56] References Cited

U.S. PATENT DOCUMENTS 2,833,801  5/1958  Holbrook .......................... 260/448.2

*Primary Examiner*—James O. Thomas, Jr.
*Assistant Examiner*—A. Siegel
*Attorney, Agent, or Firm*—Marylin Klosty

[57] ABSTRACT

Provided as novel compositions are sulfolanyloxyalkyl-heptaalkylcyclotetrasiloxanes. The cyclic polysiloxanes of the invention are especially useful as monomers for the formation of higher molecular weight polymers comprising difunctional dialkylsiloxy units in combination with difunctional sulfolanyloxyalkylmonoalkyl-siloxy units.

6 Claims, No Drawings

SULFOLANYLOXYALKYL CYCLIC POLYSILOXANES

BACKGROUND OF THE INVENTION

The present invention relates to particular organopolysiloxanes containing a sulfolanyloxyalkyl group bonded to silicon.

In accordance with the teachings of copending application Ser. No. 592,129 filed June 30, 1975, in the names of Bernard Kanner and Bela Prokai, entitled "Sulfolanyl-Bearing Organosilicone Polymers," there is provided a particular class of sulfolanyloxyalkyl-modified organopolysiloxane hydrides including those containing difunctional dialkylsiloxy units. Among other end use applications, the hydrides are useful as hydrosilation and condensation agents for the formation of sulfolanyloxyalkyl-substituted organopolysiloxane-polyoxyalkylene copolymers which are also described and claimed in said copending application. The copolymers in turn are especially useful as stabilizers of flexible polyurethane foam including foam produced with a flame-retarding agent. The present invention is concerned with a novel class of monomers which find particular application in the preparation of the aforementioned hydrides containing difunctional dialkylsiloxy units in addition to the silicon-bonded sulfolanyloxyalkyl group.

SUMMARY OF THE INVENTION

This invention provides sulfolanyloxyalkylheptaalkylcyclotetrasiloxanes as new compositions. As used herein, the term "sulfolanyloxyalkyl" refers to radicals (collectively referred to for brevity by the symbol "Q") which have the formula,

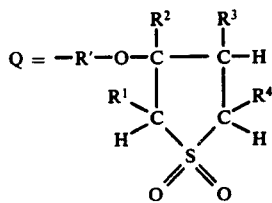

wherein: $R^1$ is bivalent alkylene of two to eight carbon atoms; and $R^1$, $R^2$, $R^3$ and $R^4$ shown bonded to the respective carbon atoms in the two to five positions of the cyclic sulfolanyl nucleus, are independently hydrogen or alkyl having from one to four carbon atoms.

More particularly, the present invention provides cyclic tetrasiloxanes having the general formula,

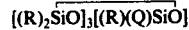

wherein: R is alkyl of one to ten carbon atoms, and Q is sulfolanyloxyalkyl, as defined above.

The Q-substituted heptaalkylcyclotetrasiloxanes described herein are useful as surface active agents for organic media and as monomers for the preparation of polymers comprising an organopolysiloxane backbone containing both dialkylsiloxy units [$(R)_2SiO_{2/2}$] and sulfolanyloxyalkylmonoalkylsiloxy units [$(R)(Q)SiO_{2/2}$].

DETAILED DESCRIPTION OF THE INVENTION AND PREFERRED EMBODIMENTS

The silicon-bonded R groups of the Q-substituted cyclic polysiloxanes of the present invention are alkyls having from one to ten carbon atoms including linear and branched alkyls. Illustrative of suitable groups encompassed by R are: methyl, ethyl, n-propyl, isopropyl, n-butyl, t-butyl, pentyl, hexyl, octyl and decyl. Of these, the lower alkyls (that is, those having from one to four carbon atoms) are preferred of which methyl is especially suitable. It is to be understood that in any given composition of the invention, the R groups may be the same as or different from one another.

In the sulfolanyloxyalkyl group (Q) of the cyclic tetrasiloxanes of the present invention, usually no more than two of $R^1$ through $R^4$ are alkyls as in the 2,4-dimethylsulfolan-3-yloxyalkyl nucleus. Preferably, each of $R^1$, $R^2$, $R^3$ and $R^4$ is hydrogen. The R' group of Q is a bivalent alkylene radical including linear and branched radicals, of the series, —$C_cH_{2c}$—, where c is an integer having a value from two to eight. Illustrative of the linear and branched saturated bivalent alkylene radicals encompassed by —R'— are the following where the valence of the carbon atom designated in the one position is satisfied by a bond to silicon of the siloxane chain, the other valence of —R'— being satisfied by the bond to oxygen of the sulfolanyloxy group of Q: ethylene; 1,3-propylene or trimethylene; 1,2-propylene; 2-methyl-1,3-propylene; 1-methyl-1,3-propylene; 1-ethyl-ethylene; 1,4-butylene or tetramethylene; 3-methyl-1,3-propylene; 3-ethyl-1,3-propylene; 1,5-pentylene or pentamethylene; 4-methyl-1,4-butylene; 1,6-hexylene or hexamethylene; 1-methyl-3,3-dimethyl-1,3-propylene; 1-ethyl-2,2-dimethyl-ethylene; 4,4-dimethyl-1,4-butylene; 3-propyl-1,3-propylene; 1-ethyl-1,4-butylene; 1-propyl-1,3-propylene; 1,8-octylene or octamethylene; and the like. Preferably, —R'— has from 2 to 6 carbon atoms and most preferably has three or four carbon atoms.

Illustrative of the sulfolanyloxyalkylmonoalkylsiloxy units [$(R)(Q)SiO_{2/2}$] of the polysiloxanes of the invention are the following:

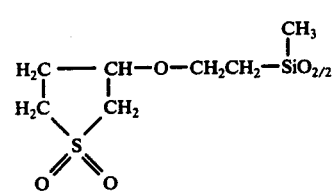

(1)

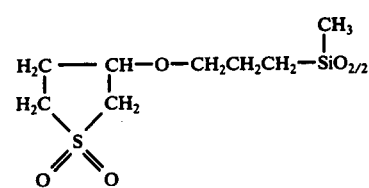

(2)

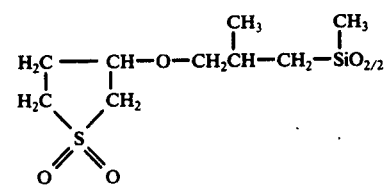

(3)

(4)

-continued

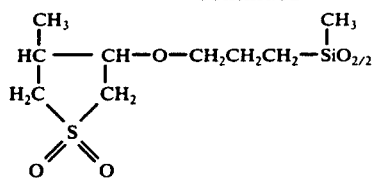

(5)

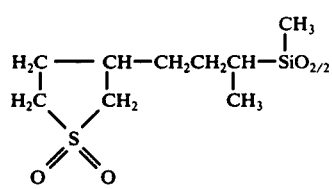

(6)

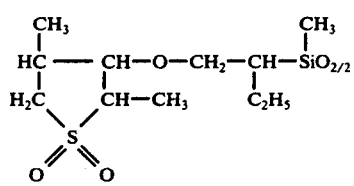

(7)

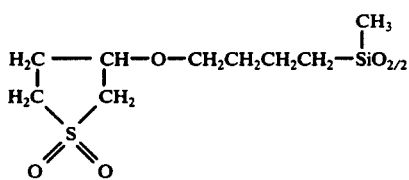

and corresponding units in which the silicon-bonded methyl group is ethyl, propyl, butyl, and the like.

The sulfolanyloxyalkylheptaalkylcyclotetrasiloxanes of the present invention may be prepared by a number of different types of reactions including hydrosilation and cohydrolsis-cocondensation reactions. One method comprises the platinum-catalyzed hydrosilation reaction between heptaalkylcyclotetrasiloxanes, [(H)(R)Si-O][(R)$_2$SiO]$_3$, and alkenyl sulfolanyl ethers as the source of the sulfolanyloxyalkyl group (Q). This reaction is shown by equation 1 which follows.

Equation 1:

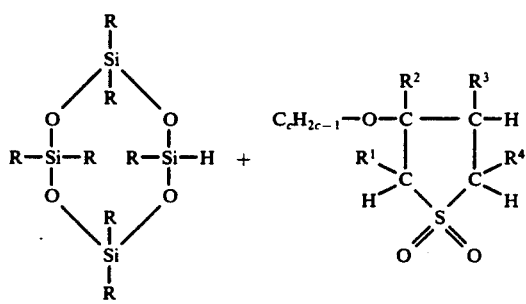

-continued

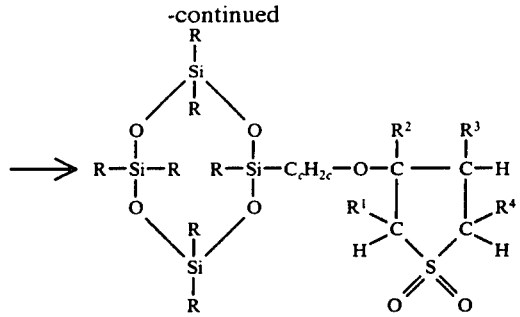

wherein: R, as previously defined, is alkyl of one to ten carbon atoms; and, as defined with respect to Q, R$^1$ through R$^4$ are hydrogen or alkyl of one to four carbon atoms and c has a value of two to eight.

Illustrative of alkenyl sulfolanyl ether reactants for use in preparing the Q-modified heptaalkylcyclotetrasiloxanes of the invention are allyl sulfolan-3-yl ether (also known as allyloxysulfolane); methallyl sulfolan-3-yl ether; crotyl sulfolan-3-yl ether; buten-3-yl sulfolan-3-yl ether; and the like. The alkenyl sulfolanyl ether reactants are prepared by the known reaction of unsaturated alcohols such as, for example, allyl and methallyl alcohols with 3-sulfolene (also known as 3-thiolene-1,1-dioxide), as described in U.S. Pat. No. 2,419,082 and British Patent Specification No. 566,930.

The preparation of the particularly preferred Q-substituted cyclic tetrasiloxanes of the invention is illustrated by the following equation 2 wherein the Si-H reactant is heptamethylcyclotetrasiloxane.

Equation 2:

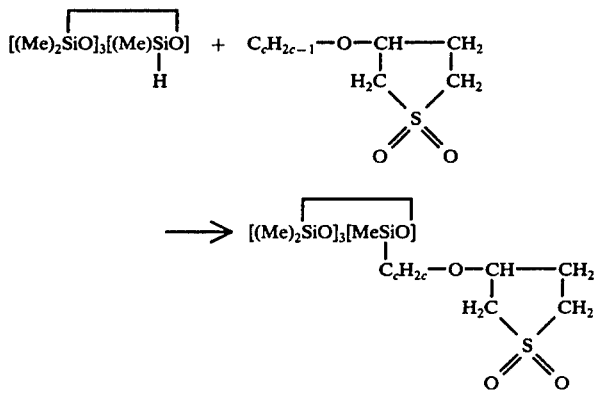

wherein Me is methyl and c has a value of three or four. For example, effecting the hydrosilation reaction of equation 2 employing 3-allyloxysulfolane, provides 3-(sulfolan-3-yloxy)propylheptamethylcyclotetrasiloxane, that is,

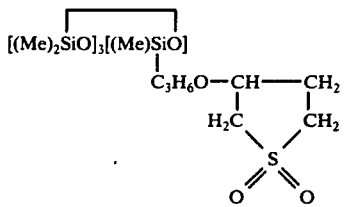

Likewise, effecting the reaction of equation 2 employing methallyl sulfolan-3-yl ether provides an adduct in which $-C_cH_{2c}-$ is 2-methyl-1,3-propylene [$-CH_2CH(CH_3)_2CH-$].

The reactions illustrated by equations 1 and 2 may be effected in the presence of any of the platinum catalysts known to the art as hydrosilation catalysts. Illustrative is platinum in the form of chloroplatinic acid is no dissolved, if desired, in a solvent such as tetrahydrofuran, ethanol, butanol, 1,2-dimethoxyethane or mixed solvents such as ethanol/1,2-dimethoxyethane. Also suitable as promoters of the hydrosilation reaction are the platinum catalysts prepared by reaction of chloroplatinic acid and an alcohol such as octanol as described in U.S. Pat. No. 3,220,972. The platinum is present in a catalytic amount such as, for example, from about 5 to about 400 parts by weight per million (p.p.m.) parts of the combined weight of the silicon-containing and organic reactants. The more usual platinum concentration is no more than about 200 p.p.m. Suitable reaction temperatures range from about room temperature (20° C.) to about 200° C., and are more usually from about 60° C. to about 160° C.

The hydrosilation reaction may be conducted in the absence or presence of a solvent. Illustrative solvents are any of the following employed individually or in combination with one another: the normally liquid aromatic hydrocarbons such as benzene, toluene and xylene; alcohols such as n-propanol and isopropanol; ethers; ether alcohols; and other such non polar or polar solvents. Upon completion of the reaction, any excess reactants and, when used, organic solvent, may be removed by conventional separation techniques to obtain the final product comprising the cyclic tetramers of the invention. It is to be understood, however, that some portion or all of the solvent and excess reactants including by-products thereof may remain in the product and that such diluted polymer compositions are also useful for the end use applications described herein. The removal or neutralization of catalyst is usually desirable for long range product stability. Neutralization is readily effected by adding sodium bicarbonate to the reaction mixture followed by filtration of the resultant slurry to remove the neutralizing agent and platinum residues.

Another method for preparing the sulfolanyloxyalkylheptaalkylcyclotetrasiloxanes of the present invention comprises cohydrolyzing and cocondensing mixtures of dialkyldichlorosilanes [i.e., $(R)_2SiCl_2$] and sulfolanyloxyalkylmonoalkyldichlorosilanes [i.e., $(Q)(R)SiCl_2$], employing about three moles of $(R)_2SiCl_2$ per mole of $(Q)(R)SiCl_2$. The latter compounds are in turn provided by the platinumcatalyzed hydrosilation of the above-described alkenyl sulfolanyl ethers as the source of Q and alkyldichlorosilanes [i.e., $(R)(H)SiCl_2$]. The cohydrolysis and cocondensation reactions may be carried out at temperatures between about 20° C. and about 150° C. in the absence or presence of a solvent such as those described above, following procedures known to the art.

The sulfolanyloxyalkylheptaalkylcyclotetrasiloxanes described herein are polymerizable to higher molecular weight Q-modified organopolysiloxanes either as essentially the sole monomer undergoing polymerization or as a comonomer with one or more precursors of polymer-building siloxy units. Such polymerizations are equilibration reactions and are accelerated by known equilibration catalysts. Self-polymerization of the sulfolanyloxyalkyl-substituted cyclic tetrasiloxanes of the present invention provides a polymeric composition consisting essentially of a polysiloxane backbone having the average empirical formula,

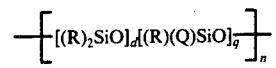

wherein: R is alkyl and Q is sulfolanyloxyalkyl as previously defined; the average value of the ratio $d:q$ is 3:1, and $n$ has an average value from about 10 to about 200. Such polymerization of the Q-substituted cyclic tetrasiloxanes of the present invention as essentially the sole monomer is accelerated by the addition of known equilibration catalysts of the acidic or basic variety. The nature of the endblocking units of the polymers formed by self-equilibration of the cyclic monomers of this invention has not been elucidated. It is postulated, however, that the polymers may comprise selfterminated macrocyclic polymeric species, linear polymeric species terminated by a siloxy linkage of a cyclic endblocker, or a combination thereof. Another explanation is that the polymers may be endblocked by an impurity introduced to the system as a component of the reactants employed in the preparation of the Q-modified cyclic monomers described herein or as a by-product formed during preparation of the cyclic monomers. It is to be understood, however, that other theories may equally explain the manner in which the self-equilibrated polymers are terminated. In any event, such self-equilibrated sulfolanyloxyalkyl-modified silicone fluids are useful as surface active agents in organic media. For example, they may be used as additives to depress the surface tension of hydrocarbon materials such as crude oil.

The sulfolanyloxyalkylheptaalkylcyclotetrasiloxanes of the present invention are also useful as monomers in forming sulfolanyloxyalkyl-substituted organopolysiloxanes in which the ratio of $(R)_2SiO:(R)$ (Q) SrO is other than 3:1, as well as sulfolanyloxyalkyl-substituted organopolysiloxanes containing other types of siloxy units. For example, acid catalyzed equilibration of a reaction medium containing:

1. cyclic dialkylsiloxane polymers as an additional source of dialkylsiloxy units $[(R)_2SiO_{2/2}]$ such as, in particular, dimethylsiloxy;

2. the Q-modified cyclic tetrasiloxanes of this invention;

3. polymeric alkylsiloxane hydrides as a source of $(R)(H)SiO_{2/2}$ units such as, in particular, $(CH_3)(H)SiO_{2/2}$; and 4. hexaalkyldisiloxanes, $(R)_3SiOSi(R)_3$, as a source of endblocking trialkylsiloxy units, $(R)_3SiO_{1/2}$, such as trimethysiloxy; provides equilibrated sulfolanyloxyalkyl-substituted polyalkylsiloxane hydrides having the following average composition,

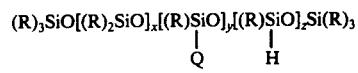

where Q and R are as previously defined herein. In the equilibrated product, the values of $x$, $y$ and $z$ are determined by the relative proportions of above reactants (1), (2) and (3) and are expressed on the normalized basis of two moles of endblocking units, $(R)_3SiO_{1/2}$. In view of the presence of reactant (1), the ratio of $x:y$ in the product is greater than 3:1. As previously disclosed herein, such sulfolanyloxyalkyl-polyalkylsiloxane hydrides are useful hydrosilation and condensation agents, and are within the teachings of the aforementioned application Ser. No. 592,129, filed June 30, 1975.

Illustrative of suitable catalysts for the equilibration of reaction mixtures containing the Q-modified cyclic tetrasiloxanes of the present invention are trifluoromethylsulfonic acid ($CF_3SO_3H$) and concentrated (93-98 weight percent) sulfuric acid. The acid is employed in a catalytically effective amount such as from about 0.1 to about four weight percent, based on the total weight of reactants. The acid-catalyzed equilibration reactions are usually carried out with vigorous mechanical stirring at temperatures within the range from about 20° C. to about 120° C. at least until the reaction mixture becomes homogeneous. Effecting the reaction at temperatures from about 20° to about 50° C. usually provides a satisfactory rate of reaction. After completion of the reaction, the reaction product is neutralized with base such as sodium bicarbonate and filtered, sometimes adding a liquid hydrocarbon such as xylene or toluene or a filter aid to facilitate the filtration. When a diluent is used, it is conveniently separated from the reaction product by rotary vacuum evaporation, as desired.

The following examples are merely illustrative of the present invention and are not intended as a limitation upon the scope thereof.

It is to be understood that in the formulas included in the data which follows, "Me" designates methyl ($—CH_3$).

EXAMPLE 1

Heptamethylcyclotetrasiloxane which had been redistilled at 83.5° C. and about 17 mm. mercury pressure was combined in an amount of 28.2 grams (0.1 mole) with about 40 ml. toluene. To this mixture there was added 3-allyloxysulfolane (17.6 grams, 0.1 mole) and about 15 ml. of toluene. The hydrosilation reaction was effected in the presence of platinum catalyst added as a four weight percent solution of chloroplatinic acid in dimethoxyethane, while heating up to a maximum temperature of 118° C. Vapor phase chromatographic analysis of a sample of the reaction mixture taken after the first 20 minutes of reaction time, indicated that the reaction had gone to greater than 50 percent completion. Heating was continued for a total reaction time of about one hour. After neutralization with sodium bicarbonate and filtration, the product was distilled to remove toluene, unreacted cyclic tetramer (3.7 grams) and a total of 8.3 grams of overhead boiling up to 128° C. and 0.3 mm. mercury pressure. In this preparation, the 3-(sulfolan-3-yloxy)propylheptamethylcyclotetrasiloxane was recovered as the residue product (22.5 grams).

EXAMPLE 2

Heptamethylcyclotetrasiloxane (141.0 grams, about 0.5 mole) was heated to 110° C. followed by the addition thereto of platinum catalyst added as a four weight percent solution of chloroplatinic acid in dimethoxyethane. A total of 78.7 grams (0.44 mole) of 3-allyloxysulfolane was added over a period of about 20 minutes during which the reaction temperature was no higher than 134° C. After the addition was completed, the temperature of the reaction mixture was 118° C. Heating at 148°-140° C. was continued for about 1.5 hours. The product was then treated with sodium bicarbonate, filter aid and activated charcoal. After allowing to stir overnight, the reaction mixture was pressure filtered and vacuum distilled. Unreacted cyclic tetramer (75.6 grams) and olefin (about 52.8 grams) was recovered. In the preparation, the product 3-(sulfolan-3-yloxy)propylheptamethylcyclotetrasiloxane, was recovered at about 150° C. and 0.8 mm. mercury pressure. After cooling, the product was retreated with activated charcoal and pressure filtered. Vapor phase chromatographic analysis of this distilled product was identical to that of the residue product of example 1 above.

The purpose of the following examples 3 and 4 is to demonstrate the use of the sulfolanyloxyalkyl-substituted cyclic tetrasiloxanes of the invention as monomers in forming sulfolanyloxyalkyl-polyalkylsiloxane hydrides.

EXAMPLE 3

In accordance with this example, a 3-(sulfolan-3-yloxy)propyl-modified polymethylsiloxane hydride was prepared by the acid-catalyzed equilibration of a reaction mixture containing the following:

Reactant (1): Hexamethyldisiloxane in an amount of 0.7 grams (0.0041 mole), corresponding to 0.0082 mole of $Me_3SiO_{2/2}$.

Reactant (2): Cyclic dimethylsiloxane tetramer in an amount of 9.7 grams, corresponding to 0.131 mole of $Me_2SiO_{2/2}$.

Reactant (3): Polymethylsiloxane hydride in an amount of 1.5 grams, corresponding to 0.025 mole of $Me(H)SiO_{2/2}$.

Reactant (4): 3-(Sulfolan-3-yloxy)propylheptamethylcyclotetrasiloxane prepared as described under Example 1, in an amount of 18.8 grams (0.041 mole), corresponding to 0.123 mole of $Me_2SiO_{2/2}$ and 0.041 mole of the 3-(sulfolan-3-yloxy)propyl-methylsiloxy unit. The reaction mixture was equilibrated in the presence of trifluoromethylsulfonic acid (2 droplets) and was allowed to stir at room temperature for approximately 22 hours. The equilibrated product was then neutralized with sodium bicarbonate, treated with activated charcoal, pressure filtered and vacuum stripped, toluene having been added to reduce the viscosity of the product and thereby facilitate filtration. The results of gel permeation chromatographic analysis indicated that equilibration had occurred. Based upon the relative proportions of Reactants (1)–(4), normalized to two moles of $Me_3SiO_{1/2}$, the average composition of the 3-(sulfolan-3-yloxy)propylmodified polymethylsiloxane hydride is:

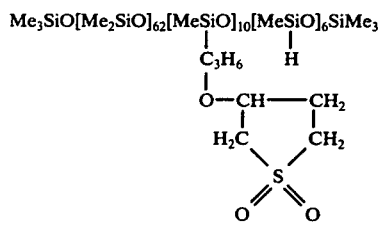

and the theoretical content of Me(H)SiO is 4.82 weight percent. Analysis of this product for silanic hydrogen provided 16.9 and 17.1 cc. $H_2$/gram, corresponding to an average found Me(H)SiO content of 4.55 weight percent which is in substantial agreement with the theoretical value.

EXAMPLE 4

In accordance with this example, a 3-(sulfolan-3-yloxy)propyl-modified polymethylsiloxane hydride was prepared by the acid-catalyzed equilibration of a reaction mixture containing the following:

Reactant (1): Hexamethyldisiloxane in an amount of 1.6 grams (0.01 mole), corresponding to 0.02 mole of $Me_3SiO_{1/2}$.

Reactant (2): Cyclic dimethylsiloxane tetramer in an amount of 38.8 grams, corresponding to 0.52 mole of $Me_2SiO_{2/2}$.

Reactant (3): Polymethylsiloxane hydride in an amount of 3.6 grams, corresponding to 0.06 mole of $Me(H)SiO_{2/2}$.

Reactant (4): 3-(Sulfolan-3-yloxy)propylheptamethylcyclotetrasiloxane prepared as described under Example 2, in an amount of 22.9 grams (0.05 mole), corresponding to 0.15 mole of $Me_2SiO_{2/2}$ and 0.05 mole of the 3-(sulfolan-3-yloxy)propyl-methylsiloxy unit. The reaction mixture was equilibrated in the presence of trifluoromethylsulfonic acid (4 droplets) while stirring at room temperature overnight. The equilibrated product was neutralized by stirring with sodium bicarbonate for about 4 hours, adding activated charcoal during the last hour. The viscous product was then pressure filtered, adding toluene to lower viscosity and thereby facilitate the filtration. After vacuum stripping, 59.5 grams of viscous product was recovered. Based upon the relative proportions of Reactants (1)–(4), normalized to two moles of $Me_3SiO_{1/2}$, the average composition of the 3-(sulfolan-3-yloxy)propyl-modified polymethylsiloxane hydride is:

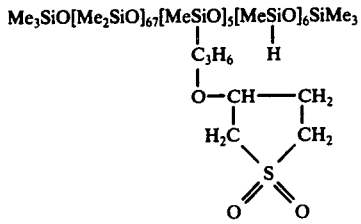

and the theoretical content of Me(H)SiO is 5.41 weight percent. Analysis of this product for silanic hydrogen provided 19.5 and 19.4 cc. $H_2$/gram, corresponding to an average found Me(H)SiO content of 5.21 weight percent which is in substantial agreement with the theoretical content.

Reaction of the respective Q-substituted polymethylsiloxane hydrides of Examples 3 and 4 in the presence of a platinum hydrosilation catalyst with an alkenyl-endblocked, organic-capped poly(oxyethylene-oxypropylene) polyether reactant such as a polyether having the average composition, $CH_2=CHCH_2(OC_2H_4)_{26.4}(OC_3H_6)_{30}OMe$, employed in an amount at least sufficient to substantially completely react the silanic hydrogen by Si-H/$CH_2=CH-$ addition, provides corresponding 3-(sulfolan-3-yloxy)propylpoly(oxyethylene-oxypropylene) block copolymers which in turn are effective stabilizers of flexible polyether polyolbased polyurethane foam.

The following example 5 illustrates a further preparation of 3-(sulfolan-3-yloxy)propylheptamethylcyclotetrasiloxane by hydrosilation of heptamethylcyclotetrasiloxane and allyloxysulfolane. The platinum catalyst employed was prepared by reacting 10 grams of chloroplatinic acid hexahydrate and 100 grams of octanol at an elevated temperature and reduced pressure, followed by removal of octanol by distillation (45° C./0.3 mm. pressure) and dissolving the residual product (35.3 grams) in toluene. As used in example 5, the expression "reduced platinum catalyst solution" refers to the resultant toluene solution of the chloroplatinic acid-octanol reaction product and contains about 0.014 gram of platinum per gram of solution which substantially corresponds to the typical 4 weight percent solution of chloroplatinic acid hexahydrate in dimethoxyethane employed in examples 1 and 2.

EXAMPLE 5

To a 100 ml. capacity reaction vessel provided with a heating mantle, mechanical stirrer, thermometer, nitrogen blow-by, addition funnel and condenser, there was added 44.7 grams of redistilled heptamethylcyclotetrasiloxane. The addition funnel contained 26.0 grams of 3-allyloxysulfolane, several ml. of toluene and 0.3 ml. of the above-described reduced platinum catalyst solution. After heating the heptamethylcyclotetrasiloxane to 95° C., the allyloxysulfolane/platinum catalyst mixture was added in increments over a period of about 35 minutes during which the reaction temperature was maintained at 96°–100° C. After this period of time, 4 droplets of additional reduced platinum catalyst solution was added. The reaction mixture was heated (maximum temperature was 122° C.) for an additional period of about 35 minutes. The product was neutralized with sodium bicarbonate, treated with filter aid and activated charcoal, pressure filtered and vacuum distilled. After separation of material boiling up to 122° C./0.9 mm. mercury pressure, product 3-(sulfolan-3-yloxy)propyl-cyclotetrasiloxane was collected at 154°–155° C. and 0.9 mm. mercury pressure in a total amount of 46.9 grams corresponding to a 70 weight percent yield, based on the allyloxysulfolane reactant. After standing for about six months, the product of this example was subjected to analysis by gel permeation chromatography. The resultant scan showed the presence of a 50:50 mixture of the 3-(sulfolan-3-yloxy)propyl heptamethylcyclotetrasiloxane and higher molecular weight polymers thereof, that is,

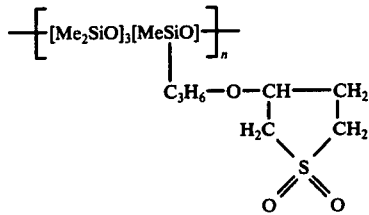

where n has an average value of about 40. The apparent ability of the cyclic tetrasiloxanes of the present invention to self-equilibrate is believed attributable to the sulfolanyl function acting as a promoter. Such self-equilibration to form higher molecular polymers is accelerated by the addition of more highly acidic equilibration catalysts such as concentrated sulfuric acid as previously described herein.

What is claimed is:

1. Sulfolanyloxyalkylheptaalkylcyclotetrasiloxanes having the general formula,

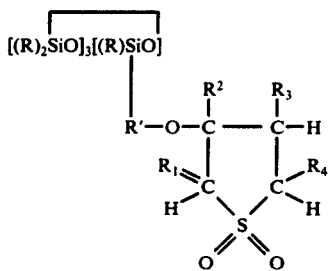

wherein: —R'— is bivalent alkylene of two to eight carbon atoms; R is alkyl of one to ten carbon atoms; and R[1], R[2], R[3] and R[4] are independently hydrogen or alkyl of one to four carbon atoms.

2. Sulfolanyloxyalkylheptaalkylcyclotetrasiloxanes having the general formula,

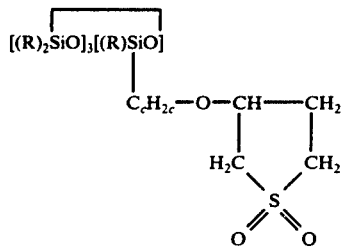

wherein: $c$ has a value from three to six; and R is alkyl of one to four carbon atoms.

3. Sulfolanyloxyalkylheptaalkylcyclotetrasiloxanes as defined in claim 2 in which —$C_cH_{2c}$— is trimethylene.

4. Sulfolanyloxyalkylheptaalkylcyclotetrasiloxanes as defined in claim 2 in which —$C_cH_{2c}$— is —$CH_2CH(CH_3)CH_2$—.

5. Sulfolanyloxyalkylheptaalkylcyclotetrasiloxanes as defined in claim 2 in which R is methyl.

6. 3-(Sulfolan-3-yloxy)propylheptamethylcyclotetrasiloxane.

* * * * *

UNITED STATES PATENT OFFICE
CERTIFICATE OF CORRECTION

Patent No. 4,049,676      Dated September 20, 1977

Inventor(s) Curtis Louis Schilling, Jr.

It is certified that error appears in the above-identified patent and that said Letters Patent are hereby corrected as shown below:

Column 3, line 42, for "cohydrolsis" read -- cohydrolysis --; lines 45-46, for the formula bridging these two lines read

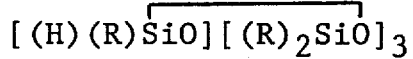

Column 4, lines 43-50, that portion of the formula reading

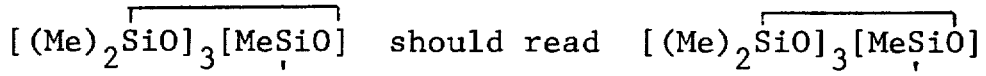

Column 5, line 6, after "acid" delete "is no".
Column 6, line 38, that portion of the formula reading SrO      should read      SiO Column 6, line 53, for "trimethysiloxy" read -- trimethylsiloxy --. Column 7, line 36, before "toluene" read -- of --. Column 8, line 3, for the first occurrence of "the" read -- this --.
Column 11; lines 1-13, that portion of the formula reading

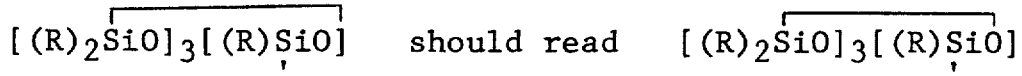

UNITED STATES PATENT OFFICE
CERTIFICATE OF CORRECTION

Patent No. 4,049,676  Dated September 20, 1977

Inventor(s) Curtis Louis Schilling, Jr.

It is certified that error appears in the above-identified patent and that said Letters Patent are hereby corrected as shown below:

and that further portion of the formula reading

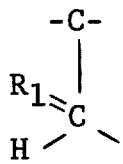   should read   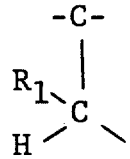

Column 12, lines 1-11, that portion of the formula reading $[(R)_2SiO]_3[(R)SiO]$   should read   $[(R)_2SiO]_3[(R)SiO]$ Signed and Sealed this Seventh Day of February 1978

[SEAL]

Attest:

RUTH C. MASON
*Attesting Officer*

LUTRELLE F. PARKER
*Acting Commissioner of Patents and Trademarks*